US00PP33105P2

(12) United States Plant Patent
Danziger

(10) Patent No.: US PP33,105 P2
(45) Date of Patent: May 25, 2021

(54) ***CALIBRACHOA* PLANT NAMED 'DCALIADR'**

(50) Latin Name: ***Calibrachoa* hybrid**
Varietal Denomination: DCALIADR

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 16/873,382

(22) Filed: Apr. 3, 2020

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
CPC ... A01H 5/02; A01H 5/00; A01H 5/12; A01H 6/82; A01H 6/821; A01H 6/14
See application file for complete search history.

(56) References Cited

PUBLICATIONS

Danziger Lia Dark Red, retrieved on Sep. 9, 2020, retrieved from the Internet at https://www.danzigeronline.com/variety/lia-dark-red/, 3 pp. (Year: 2020).*

Leo Berbee Bulb Co.Fall 2019—Spring 2020 Plantpeddler Young Plants, retrieved on Sep. 9, 2020, retrieved from the Internet at https://www.berbeeyoungplants.com/catalog/Fall%2019-%20Spr%2020%20BP%20product%20pages.pdf, pp. 1,33. (Year: 2019).*

* cited by examiner

*Primary Examiner* — June Hwu
(74) *Attorney, Agent, or Firm* — Cassandra Bright

(57) ABSTRACT

A new and distinct *Calibrachoa* cultivar named 'DCALIADR' is disclosed, characterized by a controlled, mounded to semi-trailing plant habit and large dark red flowers. Plants produce dark green foliage and have moderate vigor. The new variety is a *Calibrachoa*, normally produced as an outdoor garden or container plant.

2 Drawing Sheets

Figure 1:
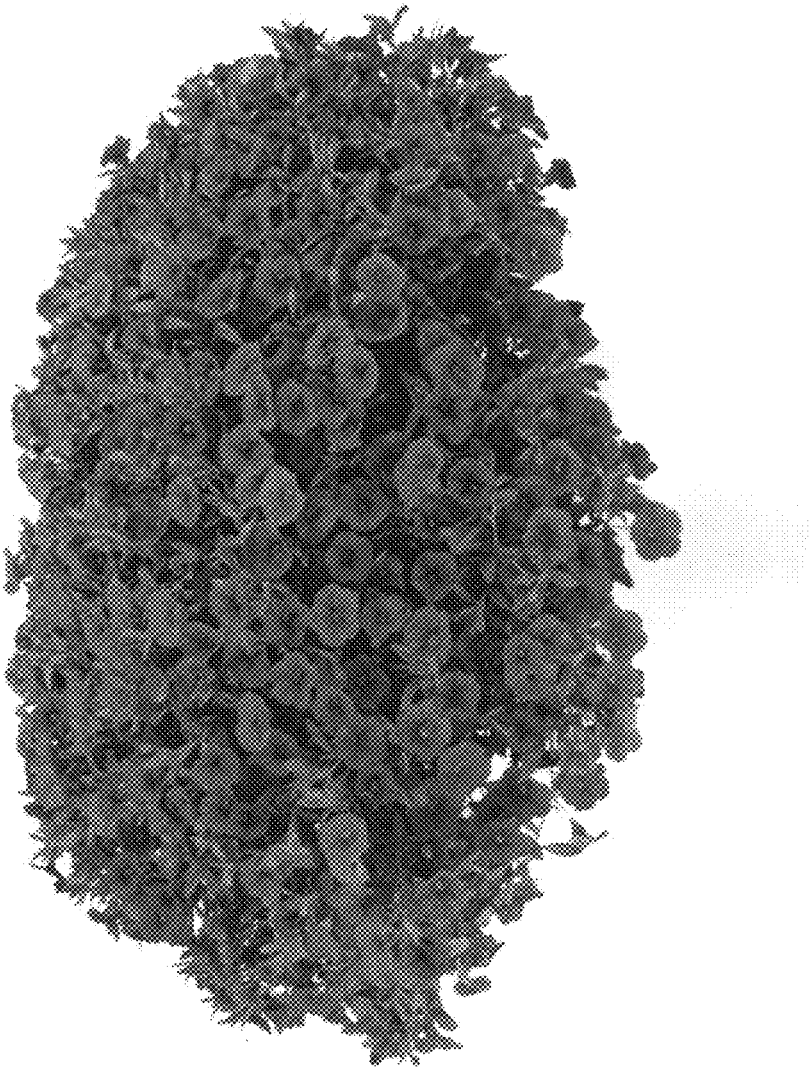

Latin name of the genus and species: *Calibrachoa* hybrid.
Variety denomination: 'DCALIADR'.

BACKGROUND OF THE INVENTION

The new *Calibrachoa* cultivar is a product of a planned breeding program conducted by the inventor, Gavriel Danziger in Moshav Mishmar Hashiva, Israel. The objective of the breeding program was to produce new *Calibrachoa* varieties for ornamental purposes. The open pollination resulting in this new variety was made during March of 2016.

The seed parent is the unpatented, propriety variety referred to as *Calibrachoa* 'CA. 16-5018'. The pollen parent is unidentified. The new variety was discovered in March of 2017 by the inventor in a group of seedlings resulting from the open pollination, in a research greenhouse in Moshav Mishmar Hashiva, Israel.

Asexual reproduction of the new cultivar 'DCALIADR' was first performed by terminal vegetative cuttings during March of 2017, at a greenhouse in Moshav Mishmar Hashiva, Israel. Subsequent propagation by has shown that the unique features of this cultivar are stable and reproduced true to type in successive generations. Date of first sale was Apr. 7, 2019, occurring in the United States. This sale was made directly by the inventor or one who obtained the claimed invention directly or indirectly from the inventor. This sale and all public disclosures made between Apr. 7, 2019 and the filing of this application fall within the exception allowed under 102(b)(1).

SUMMARY OF THE INVENTION

The cultivar 'DCALIADR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCALIADR' These characteristics in combination distinguish 'DCALIADR' as a new and distinct *Calibrachoa* cultivar:

1. Large dark red flowers.
2. Early flowering.
3. Dark green foliage.
4. Controlled, mounded to semi-trailing plant habit.
5. Moderate vigor.

PARENT COMPARISON

Plants of the new cultivar 'DCALIADR' are similar to plants of the seed parent in most horticultural characteristics, however, plants of the new cultivar 'DCALIADR' differ in the following;

1. The new variety has a mounded to semi-trailing growth habit; the seed parent has a trailing plant habit.
2. The new variety has dark red flowers; seed parent has dark pink flowers.
3. The new variety has larger flowers than the seed parent.
4. The seed parent has lighter green foliage than the new variety.
5. The new variety forms a fuller plant than the seed parent which has an empty center.

COMMERCIAL COMPARISON

Plants of the new cultivar 'DCALIADR' can be compared to the patented commercial variety *Calibrachoa*

'KLECA17038' U.S. Plant Pat. No. 30,835. These varieties are similar in most horticultural characteristics; however, 'DCALIADR' differs in the following:

1. 'DCALIADR' has a darker red flower color than this comparator.
2. 'DCALIADR' is less susceptible to powdery mildew than this comparator.
3. 'DCALIADR has a bigger flower than 'KLECA17038'.
4. 'DCALIADR' has a more vigorous growth habit than this comparator.

Plants of the new cultivar 'DCALIADR' can also be compared to the commercial variety *Calibrachoa* 'Red Lips' (unpatented). These varieties are similar in most horticultural characteristics; however, 'DCALIADR' differs in the following:

1. 'DCALIADR' is a darker red flower color than this comparator.
2. 'DCALIADR' has a more mounded plant habit than 'Red Lips'.
3. 'DCALIADR' has darker green foliage than 'Red Lips'.
4. 'DCALIADR' is less vigorous than 'Calitastic Red'.

BRIEF DESCRIPTION OF THE PHOTOGRAPHS

The accompanying photograph in FIG. 1 illustrates in full color a typical plant in a 20 cm pot, at approximately 5 months of age, of 'DCALIADR' grown in a greenhouse, in Moshav Mishmar Hashiva, Israel.

Figure 2:
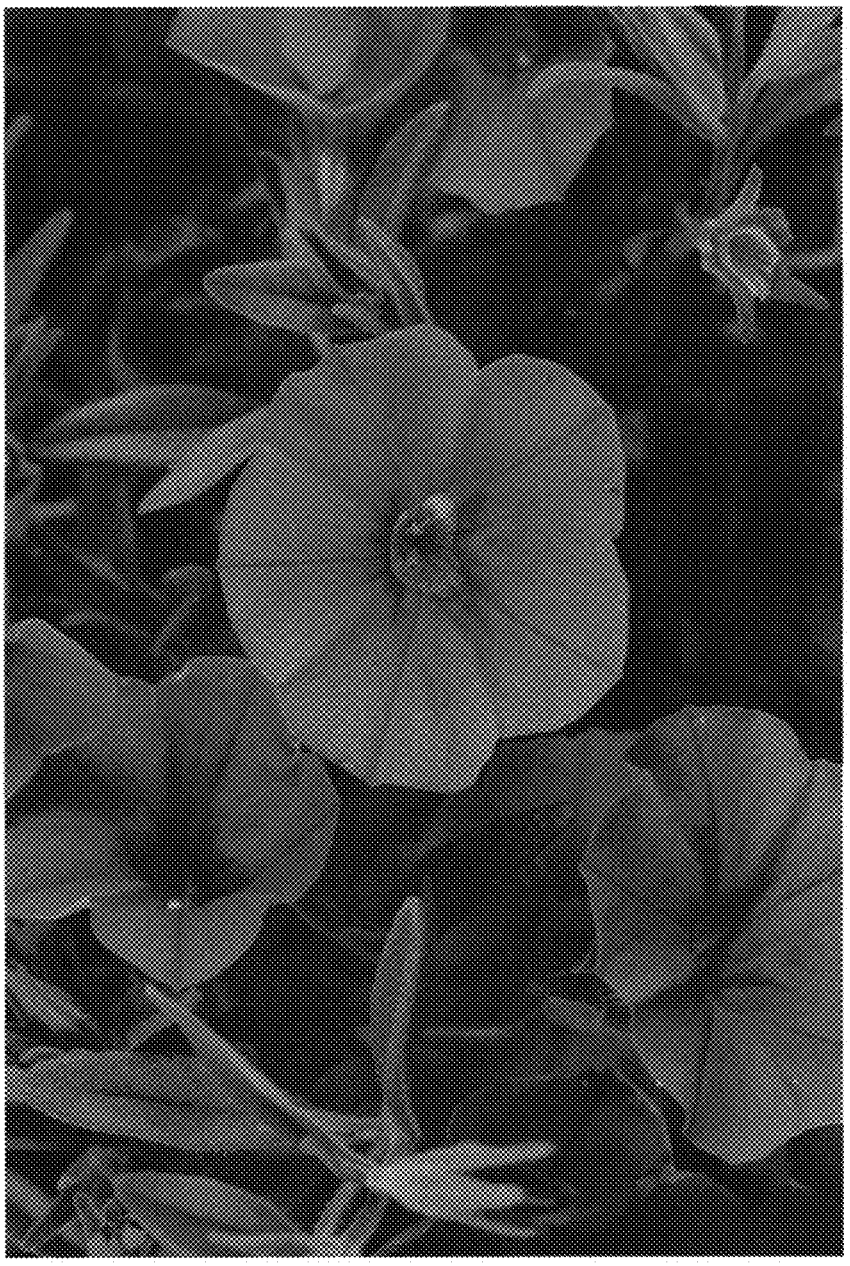

FIG. 2 illustrates in full color a close-up view of flowers of 'DCALIADR'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCALIADR' plants grown in greenhouse in Moshav Mishmar Hashiva, Israel, under natural lighting. Measurements were taken during Summer of 2018. The plants were approximately 60 days from a rooted cutting in a 13 cm pot. The growing temperature ranged from 16° C. to 30° C. during the days, 8° C. to 20° C. during the nights. Measurements and numerical values represent averages of typical plant types.

Botanical classification: *Calibrachoa* hybrid 'DCALIADR'.

PROPAGATION

Time to initiate roots: 10 to 15 days at approximately 18° C.
Root description: Fibrous.

PLANT

Growth habit: Mounded to semi-trailing.
Pot size of plant described: 13 cm.
Height: About 12 cm to top of flowering plane.
Plant spread: 37 cm.
Growth rate: Moderate.
Length of primary lateral branches: 16 cm.
Diameter of lateral branches: 3-4 mm.
Quantity of primary lateral branches: 13.
Characteristics of primary lateral branches:
*Form.*—Cylindrical.
*Diameter.*—3-4 mm.
*Color.*—Near RHS Yellow-Green 146C. Terminal branch ends flushed near Purple N79B.
*Texture.*—Pilose.
*Strength.*—Strong, flexible.
Internode length: 1 to 1.3 cm.

FOLIAGE

Leaf:
*Arrangement.*—Alternate.
*Quantity.*—Approximately 1000 per plant.
*Average length.*—3 cm.
*Average width.*—9 mm.
*Shape of blade.*—Elliptic.
*Apex.*—Rounded.
*Base.*—Acuminate.
*Margin.*—Entire.
*Texture of top surface.*—Pubescent.
*Texture of bottom surface.*—Scabrous.
*Aspect.*—45 degrees from branch, slightly arched.
*Color.*—Young foliage upper side: RHS Green 137A. Young foliage under side: RHS Green 137C. Mature foliage upper side: RHS Green 137A. Mature foliage under side: RHS Green 137B. Venation: Type: Pinnate. Venation color upper side: RHS Green 137A. Venation color under side: RHS Green 137B.
*Petiole.*—Length: 2-3 mm. Diameter: 1.5-2.0 mm. Color: RHS Green 137B. Texture: Pubescent.

FLOWER

Natural flowering season: Spring to Autumn,
Days to flowering from rooted cutting: About 30 days.
Inflorescence and flower type and habit: Axillary, single flower, salverform shape, upward and outwardly facing.
Rate of flower opening: 2 to 3 days from bud to fully opened flower.
Flower longevity on plant: 4 to 7 days.
Approximate quantity of flowers per plant: About 90.
Persistent or self-cleaning: Self-cleaning.
Bud:
*Shape.*—Ovoid.
*Length.*—8-9 mm.
*Diameter.*—5 mm.
*Color.*—RHS Green 138B.
Flower size:
*Diameter.*—4.5 cm.
*Length.*—4.0 cm.
*Flower tube diameter at distal end.*—1.5 cm.
*Flower tube diameter at proximal end.*—7 mm.
Petals:
*Length from throat.*—2.0 cm.
*Width.*—2.2 cm.
*Quantity.*—5.
*Lobing.*—Weak.
*Texture.*—Glabrous.
*Apex.*—Truncate.
*Margin.*—Entire.
Color:
*When opening.*—Upper surface: Near RHS Red 53A, center flushed Greyed-Purple N187A. Lower surface: Near RHS Red 53C.

*Fully opened.*—Upper surface: Near RHS Red 53A. Lower surface: Near RHS Red 53C. Flower throat (inside): RHS Yellow-Orange 14B. Small, partially rounded transitional coloration of Red 53A. Flower throat, vein: RHS Grey RHS Red 53A. Flower tube (outside): RHS Yellow-Orange 14D. Flower tube, vein: RHS Greyed-Orange 177A. Petal color, fading to: RHS Red 53C. Conspicuousness of veins, throat and outer corolla tube: Weak.

Calyx/sepals:

*Quantity per flower.*—5.

*Shape.*—Lanceolate.

*Length.*—1.5 cm.

*Width.*—5 mm.

*Apex.*—Rounded.

*Base.*—Cuneate.

*Margin.*—Entire.

*Texture.*—Pubescent.

*Color.*—Upper Surface: RHS Green 138A. Lower Surface: RHS Green 138B.

Peduncle: None present.

Pedicel:

*Length.*—0.8-1.2 cm.

*Diameter.*—0.15 cm.

*Color.*—RHS Green 138B.

*Orientation.*—45 degrees.

Fragrance: None.

REPRODUCTIVE ORGANS

Stamens:

*Number.*—5.

*Filament length.*—3-9 mm.

Anthers:

*Length.*—1 mm.

*Shape.*—Globose.

*Color.*—RHS Yellow 13C.

*Pollen.*—Color: RHS Yellow 12C. Quantity: Moderate.

Pistil:

*Number.*—1.

*Length.*—6 mm.

*Style.*—Length: 4.5 mm. Color: RHS Yellow-Green 145B.

*Stigma.*—Shape: Oblate. Color: RHS Yellow-Green 145A. Ovary Color: RHS Yellow-Green 145C.

OTHER CHARACTERISTICS

Seeds and fruits: About 30 dark brown, rounded seeds of about 0.5 mm diameter, per one brown, conical capsule.

Disease/pest resistance: Some observed resistance to *Podosphaera xanthii*. No additional resistance nor susceptibility to the normal diseases and pests of *Calibrachoa* have been observed. Pests common to *Calibrachoa* include Aphids and thrips. Typical diseases are *Botrytis* and *Pythium*.

Temperature tolerance: 5° C. to 30° C.

Drought tolerance: No tolerance for drought.

What is claimed is:

1. A new and distinct cultivar of *Calibrachoa* plant named 'DCALIADR' as herein illustrated and described.

* * * * *